United States Patent
Watrous

(10) Patent No.: US 8,690,789 B2
(45) Date of Patent: Apr. 8, 2014

(54) CATEGORIZING AUTOMATICALLY GENERATED PHYSIOLOGICAL DATA BASED ON INDUSTRY GUIDELINES

(75) Inventor: Raymond L. Watrous, Belle Mead, NJ (US)

(73) Assignee: 3M Innovative Properties Company, St. Paul, MN (US)

( * ) Notice: Subject to any disclaimer, the term of this patent is extended or adjusted under 35 U.S.C. 154(b) by 387 days.

(21) Appl. No.: 13/103,750

(22) Filed: May 9, 2011

(65) Prior Publication Data

US 2011/0208080 A1 Aug. 25, 2011

Related U.S. Application Data

(62) Division of application No. 11/500,871, filed on Aug. 8, 2006, now abandoned.

(51) Int. Cl.
*A61B 5/00* (2006.01)

(52) U.S. Cl.
USPC .......................................................... 600/528

(58) Field of Classification Search
USPC .......................................................... 600/528
See application file for complete search history.

(56) References Cited

U.S. PATENT DOCUMENTS

| | | | |
|---|---|---|---|
| 6,053,872 A * | 4/2000 | Mohler | 600/485 |
| 6,112,021 A * | 8/2000 | Brand | 703/2 |
| 6,572,560 B1 | 6/2003 | Watrous | |
| 6,629,937 B2 | 10/2003 | Watrous | |
| 6,725,190 B1 | 4/2004 | Chazan | |
| 6,898,459 B2 | 5/2005 | Hayek | |
| 6,953,436 B2 | 10/2005 | Watrous | |
| 2004/0092846 A1 | 5/2004 | Watrous | |
| 2004/0230105 A1 | 11/2004 | Geva | |
| 2004/0260188 A1 | 12/2004 | Syed | |
| 2005/0245973 A1 | 11/2005 | Sherman | |
| 2006/0047213 A1 | 3/2006 | Gavriely | |
| 2006/0161064 A1 | 7/2006 | Watrous | |

OTHER PUBLICATIONS

Watrous et al. "Computer-Assisted Detection of Systolic Murmurs Associated with Hypertrophic Cardiomyopathy" Texas Heart Institute Journal 2004;31:368-375.*

Gamero et al. "Detection of the First and Second Heart Sound Using Probabilitstic Models" Proc of 25th Annual International Conference of IEEE EMBS, 2003;25:2877-2880.*

Bonow, "Guidelines for the Management of Patients With Valvular Heart Disease: Executive Summary: A Report of the American College of Cardiology/American Heart Association Task Force on Practice Guidelines (Committee on Management of Patients with Valvular heart Disease)", Journal of the American Heart Association, Circulation 1998, pp. 1949-1984.

El-Asir, "Multiresolution Analysis of Heart Sounds Using Filter Banks", Information Technology Journal, vol. 3, No. 1, 2004, pp. 36-43.

\* cited by examiner

*Primary Examiner* — Luther Behringer

(57) ABSTRACT

Methods and systems for mapping a physiological signal into clinical guideline parameters are disclosed. A physiological signal having a characteristic that may represent an anomaly is received and mapped to a clinical guideline condition space. Probabilities are determined that the mapped signal with which the anomaly may be associated represents a first clinical guideline condition corresponding to a referral indication or a second clinical guideline condition corresponding to an absence of the referral indication. The determined probability is presented and a referral decision is made responsive to the determined probability that the anomaly is associated with the first clinical guideline condition.

11 Claims, 9 Drawing Sheets

CATEGORIZING AUTOMATICALLY GENERATED PHYSIOLOGICAL DATA BASED ON INDUSTRY GUIDELINES

CROSS REFERENCE TO RELATED APPLICATIONS

This application is a divisional of application Ser. No. 11/500,871, filed Aug. 8, 2006, now pending, the disclosure of which is incorporated by reference in its entirety herein.

FIELD OF THE INVENTION

The present invention relates to categorizing physiological data in general and, specifically, to systems and methods for mapping heart sounds to clinical guideline referral conditions.

BACKGROUND OF THE INVENTION

A wide variety of medical diagnostic decision support systems are used in health care. These systems can generally record and process physiological data to present physiological features to assist a health care professional in determining the presence of a pathophysiological condition. One example of a medical diagnostic support system is an auscultation system that extracts features from a phonocardiogram. These auscultatory features are known in clinical practice and are readily understood by practicing physicians. Examples of such auscultatory features include the first heart sound (S1), second heart sound (S2), third heart sound (S3), fourth heart sound (S4), heart murmurs, S2 splitting, ejection sounds, opening snaps, and midsystolic clicks.

An objective of deriving physiological features such as auscultatory features is to provide the health care professional, such as a physician, with accurate information that can be used in making a diagnostic decision. At the primary care level, this typically depends on whether the physiological features are indicative of a condition necessitating a referral to a specialist for further evaluation.

Medical diagnostic decision support systems may attempt to identify specific features that are indicative of a specific pathophysiological condition. An auscultatory system, for example, may identify specific properties of a phonocardiogram that are consistent with a specific cardiovascular disease. This auscultatory system may be developed with the expectation that the physician would then refer for further evaluation patients with heart sounds that are generated by pathophysiological conditions.

The relationship between features extracted from physiological data and a diagnosis of a pathophysiological condition, however, is complex. It may be desirable to take into account additional information about the patient, such as medical history, symptoms, vital signs and the results of other tests, such as an X-Ray, electrocardiogram (EKG) in order to make a referral decision. By incorporating additional information, a physician may be better equipped to diagnose a pathophysiological condition, particularly if one of the examined features provides conflicting information as compared to the additional information. The additional information may be used to help reduce unnecessary referral decisions. It may also be desirable to automate a portion of the analysis used by physicians to make a referral decision. In this manner, a number of different information sources may be analyzed, integrated and presented to the physician for referral review.

SUMMARY OF THE INVENTION

The present invention is embodied in a method for mapping a physiological signal into clinical guideline parameters. The method receives a physiological signal. The physiological signal has a characteristic that may represent an anomaly. The method maps the received physiological signal to a clinical guideline condition space. The method further determines a probability that the mapped signal with which the anomaly is associated represents one of a first clinical guideline condition corresponding to a referral indication or a second clinical guideline condition corresponding to an absence of the referral indication. The method also presents the determined probability to a user.

The present invention is further embodied in a method for mapping a physiological signal into clinical guideline parameters for distinguishing between a first condition corresponding to a referral indication and a second condition corresponding to an absence of the referral indication. The method receives the physiological signal. The physiological signal including a characteristic that that may contain an anomaly representing a referral indication. The anomaly is within at least one physiological event of the physiological signal. The method also computes a normalized energy profile for the at least one physiological event representative of the anomaly and maps the normalized energy profile to a clinical guideline condition space. The method also determines probabilities that the mapped normalized energy profile is associated with each of the first condition and the second condition and presents the determined probabilities.

The present invention is further embodied in a method for assisting in a referral indication of heart murmurs. The method receives an acoustic signal representing heart sounds and parses the received acoustic signal into physiological events including a plurality of systolic intervals and a plurality of diastolic intervals. The method further computes a first normalized mid-range energy representative of a median systolic interval and a second normalized mid-range energy representative of a median diastolic interval, respectively. The first and second normalized mid-range energies are computed from the parsed acoustic signal. The method also characterizes the median systolic interval based on the first normalized mid-range energy. The method further determines probabilities relative to a first condition associated with the referral indication and a second condition associated with an absence of the referral indication based on the characterized median systolic interval. The method further presents the first normalized mid-range energy, the second normalized mid-range energy and the determined probabilities. The presented first normalized mid-range energy, the second normalized mid-range energy and the determined probabilities may be used to determine whether a referral is indicated.

The present invention is further embodied in a system for mapping a heart sound signal to clinical guideline referral indicators. The system includes an input terminal for receiving the heart sound signal comprising systolic intervals and diastolic intervals and a murmur detector for computing a statistic that a murmur is present from the heart sound signal. The system further includes a normalized mid-range energy calculator for computing a normalized mid-range energy profile from the heart sound signal. The normalized mid-range energy profile is representative of a median systolic interval of the heart sound signal. The system further includes a clinical guideline referral converter for mapping the normalized mid-range energy profile to a first clinical guideline condition associated with a referral indication and a second clinical guideline condition associated with an absence of the referral indication and determining probabilities that the normalized mid-range energy profile is associated with the first or the second clinical guideline conditions. The system further includes a display for displaying the normalized mid-range energy profile, the murmur detection statistic, and the determined probabilities.

The present invention is further embodied in a display for a clinical device. The display includes a first normalized mid-range energy profile associated with a median systolic interval of a heart sound signal and a second normalized mid-range energy profile associated with a median diastolic interval of the heart sound signal. The display also includes at least one probability indicator which indicates that the median systolic interval represents a first clinical guideline condition associated with a referral indication and a second clinical guideline condition associated with an absence of the referral indication. The display further includes murmur detection indicators indicating the detection of murmurs in the heart sound signal.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

There are known diagnostic decision support systems which attempt to diagnose a pathophysiological condition or to diagnose a likelihood of a pathophysiology on the basis of a single physiological signal. It is desirable, however, for a decision support system that does not attempt to develop a diagnosis based on a physiological signal but instead analyzes features of the physiological signal to provide data that can be integrated by a physician along with other patient information that is relevant to making a diagnosis or referral decision.

In the art there are known industry referral guidelines, such as guidelines established by the American College of Cardiology (ACC) and American Heart Association (AHA) ACC/AHA which provide a physician with recommendations for making a referral decision. It is thus desirable to provide a diagnostic decision support system that presents analyzed features in accordance with industry guidelines such as ACC/AHA guidelines. In this manner, the physician may follow the industry guidelines to make a referral decision.

Figure 1:
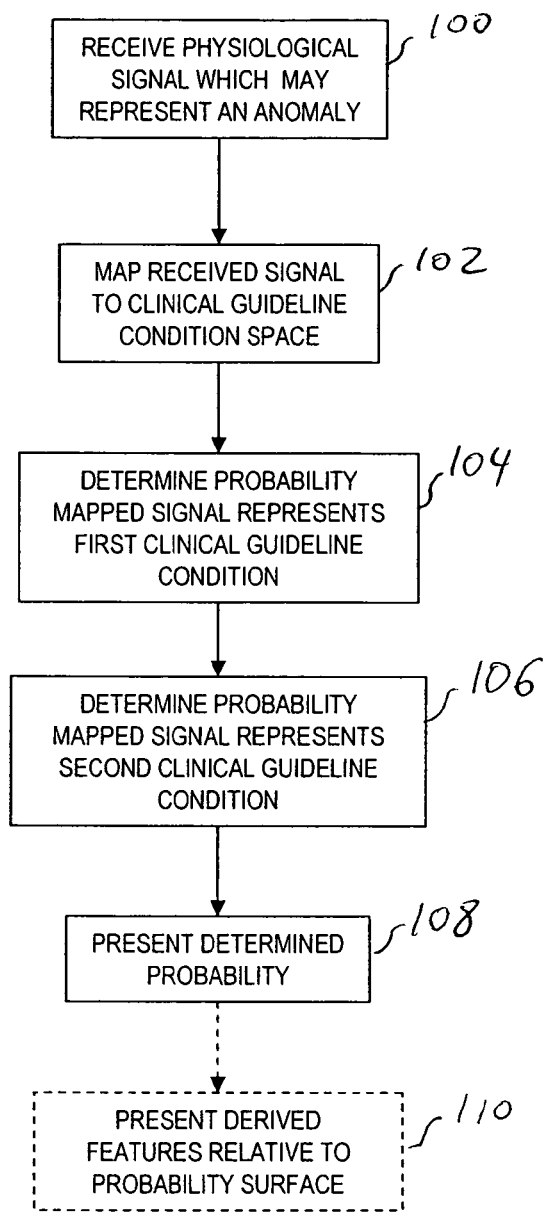
FIG. 1 is a flowchart illustrating an exemplary method for mapping a physiological signal into clinical data according to an aspect of the present invention.

FIG. 1 shows a flowchart illustrating an exemplary method for mapping a physiological signal to clinical guideline parameters according to the present invention. In step 100, physiological data is received. The physiological data may have a characteristic that indicates an anomaly, for example a systolic murmur. In step 102, the received physiological signal is mapped to a clinical guideline condition space. The clinical guideline condition space is desirably associated with predetermined clinical guidelines, i.e. indications, for a condition related to the anomaly developed to assist a physician with making a referral decision. In step 104, a probability is determined that the mapped physiological signal represents a first clinical guideline condition. This condition is associated with a referral guideline condition. In step 106, a probability is determined that the mapped physiological signal represents a second clinical guideline condition. This second condition is associated with an absence of a referral condition. In step 108, the resulting probabilities are presented. The second condition may also be associated with indications that a referral is not advisable. For example, if a mid-systolic murmur is detected having less than grade 2 loudness and no other significant auscultatory features, this may represent a functional murmur where a referral is not advisable. In alternate step 110, derived features may be presented relative to a predetermined probability surface. The derived features relate to the clinical guideline space and thus allow a physiological signal to be mapped to a space over which clinical guidelines are interpretable.

In an exemplary embodiment, ACC/AHA clinical guidelines by Bonow et al. entitled "ACC/AHA guidelines for the management of patients with valvular heart disease: executive summary. A report of the American College of Cardiology/American Heart Association Task Force on Practice Guidelines (Committee on Management of Patients with Valvular heart Disease) published *Circulation* in 1998 are used as the clinical guideline space for determining whether to refer an asymptomatic patient for evaluation by echocardiography when that patient has a murmur of unknown origin. These ACC/AHA guidelines are written in terms of three classes which vary in expected efficacy and safety for an echocardiogram referral (herein echo).

In an exemplary embodiment, heart sound signals are of interest. The heart sound signal may be separated into repeatable physiological events, typically the first heart sound, S1, caused by the closing of the atrioventricular valves, followed by the second heart sound, S2, caused by the closing of the semilunar valves. Intervals of interest are the systolic interval, defined from the end of S1 to the onset of S2, and the diastolic interval, defined from the end of S2 to the onset of S1.

In a first condition according to the present invention, i.e. a class I condition, there is evidence and/or general agreement that a given procedure or treatment is useful and effective.

Patients with murmurs that have certain well-defined auscultatory findings, according to the ACC/AHA guidelines, described below, fall into the first condition, where evaluation by echo is deemed useful and effective.

In a second condition according to the present invention, i.e. a class III condition, there is evidence and/or general agreement that the procedure/treatment is not useful and in some cases may be harmful. Asymptomatic patients with other well-defined auscultatory features, according to the ACC/AHA guidelines, described below, fall into the second condition.

In a further condition, i.e. class II according to clinical guideline standards, conditions exist for which there is conflicting evidence and/or a divergence of opinion about the usefulness/efficacy of a procedure or treatment. Class II can be further separated into a class IIa and class IIb. Under class IIa, the weight of evidence/opinion is in favor of usefulness/efficacy. Under class IIb, the usefulness/efficacy is less well established by evidence/opinion. The present invention does not distinguish class II conditions. Rather, the present invention maps the physiological signal to the class I (first condition) and class III (second condition) space. A physician can then interpret the probability findings as well as other presented information to help distinguish class II conditions. Class II conditions may correspond to findings that are not related to auscultation, and may be derived from sensors. For example, murmurs associated with abnormal EKG use EKG sensors to distinguish murmurs in this class. It is contemplated, however, that the present invention may also distinguish Class II conditions by incorporating other input information and class II condition guideline parameters into an exemplary method as described below.

The ACC/AHA have assigned diastolic or continuous murmurs to the first condition. In addition, holosystolic or late systolic murmurs meet with the first condition. Finally, mid-systolic murmurs having a grade 3 or higher loudness are also assigned to the first condition.

The ACC/AHA have assigned midsystolic murmurs of grade 2 or lower loudness identified as innocent or functional by an experienced observer to the second condition. The guidelines further stipulate that such innocent murmurs have the following characteristics: a grade 1 to 2 intensity at the left sternal border, a systolic ejection pattern, a normal intensity and splitting of the second heart sound, no other abnormal sounds or murmurs, no evidence of ventricular hypertrophy or dilation and the absence of increased murmur with the Valsalva maneuver.

According to the ACC/AHA guidelines, a murmur profile (early, mid, late, holo) and/or murmur loudness are used to distinguish between the first condition and the second condition in the case of systolic murmurs. In an exemplary embodiment of the present invention, a murmur energy for the systolic interval is desirably used to map the auscultatory signal to the clinical guideline condition space. It is noted that the presence of a continuous or diastolic murmur is evidence of the first condition and a further mapping may not be needed to support the ACC/AHA guidelines.

Murmur energy for the diastolic interval, however, as well as a combination of the systolic and diastolic interval, for continuous murmurs, may be used to map the acoustic signal to a first predetermined condition space and a second predetermined condition space. The first and second predetermined condition spaces may be associated with murmur energy and non-murmur energy, respectively. It is contemplated that the second condition space may be associated with nonreferrable murmur energy, for example, the nonreferrable murmur energy may correspond to an innocent murmur. The murmur energy may be associated with continuous and/or diastolic murmurs. The first and second condition spaces may be determined from signals having known diastolic and/or continuous murmurs and signals not including diastolic and/or continuous murmurs.

Although an exemplary embodiment illustrates computing an energy profile of heart murmurs, it is contemplated that the present invention may be used with other physiological data. For example low frequency heart sounds such as S3 and S4 may be determined from an energy measure. These sounds are typically in the range of 50-90 Hz making them difficult to detect by a physician using standard auscultatory practices. Other physiological sounds may include peristaltic sounds such as renewal for bowel action post-surgery and lung sounds for characterizing crackles and wheezes. The present invention may be used with any physiological sound where an energy profile of a physiological feature may be used to map the sound into a guideline space.

Figure 2:
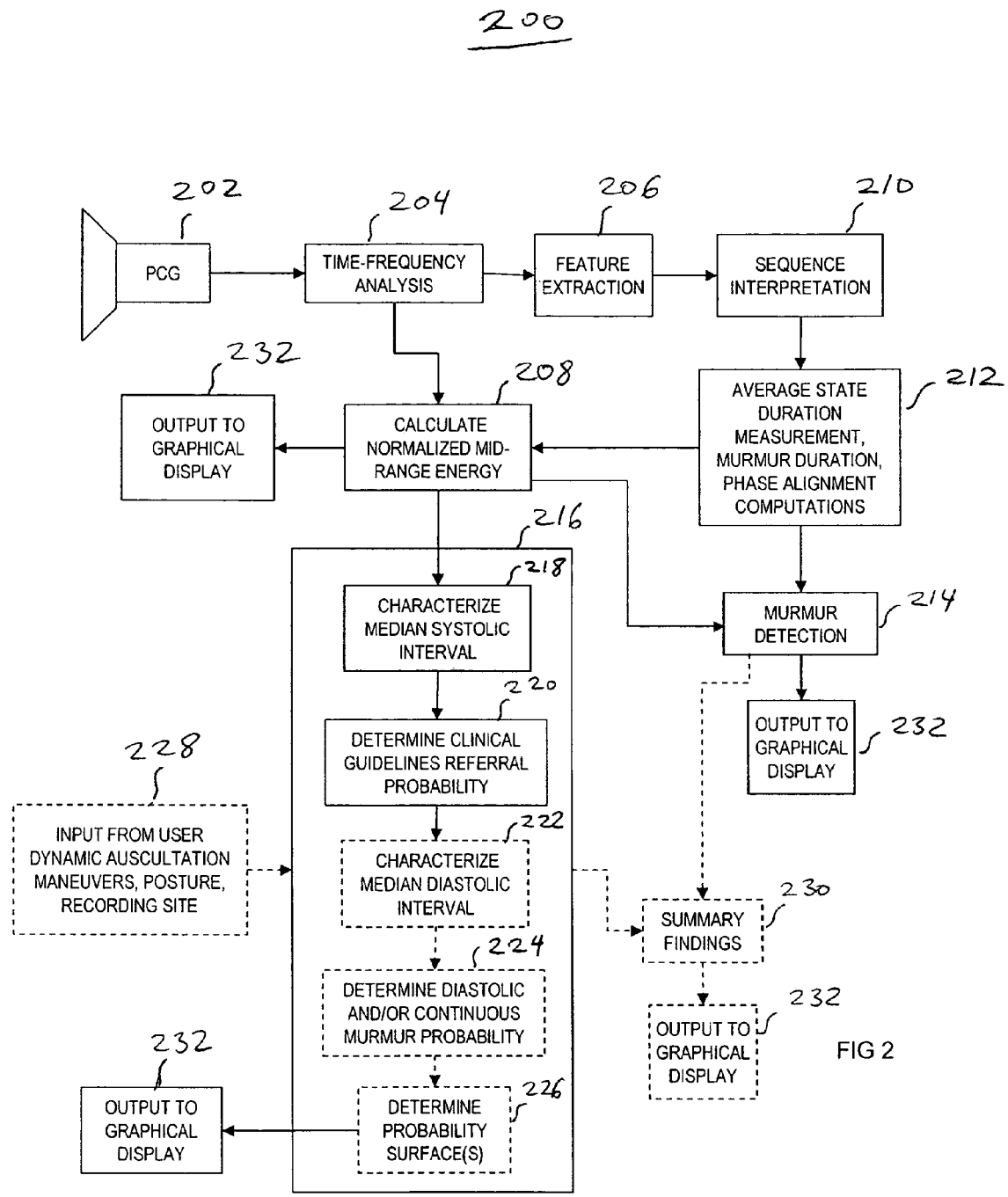
FIG. 2 is a functional block diagram illustrating an exemplary system for mapping heart sound signals to clinical guideline referral indicators according to an aspect of the present invention.

FIG. 2 is a functional block diagram of an exemplary system 200 for mapping heart sound signals to clinical guideline referral indicators according to the present invention. The system shown in FIG. 2 includes many of the elements of the system described in U.S. Pat. Nos. 6,572,560 and 6,953,436 entitled MULTI-MODAL CARDIAC DIAGNOSTIC DECISION SUPPORT SYSTEM AND METHOD, which describes cardiac diagnostic systems.

The present invention, however, includes additional features related to the mapping of heart sounds to clinical guideline referral indicators based on analysis of mid-range energy in acoustic heart signals. In exemplary system 200, heart sounds are detected by phonocardiograph instrument (PCG) 202, which may be, for example, an electronic stethoscope. Output signals provided by PCG 202 may be amplified and filtered by a preamplifier, filter or any combination thereof (not shown) to increase the amplitude of signals that are in a range of frequencies corresponding to heart sounds while attenuating signals outside of that frequency range. The preamplification and/or filtering may be performed within PCG 202.

Time-frequency analysis circuit 204 receives the signals provided by PCG 202 and analyzes these signals using, for example, a wavelet decomposition to extract frequency information from the signal. Although an exemplary embodiment described below employs a wavelet transform and a Morlet wavelet, it is contemplated that other time-frequency analysis methods may be used and that other wavelets may be used. The wavelet decomposition is desirably scaled to compensate for variations in amplitude of the acoustic heart sounds provided by PCG 202. The wavelet decomposition may be sampled logarithmically. In an exemplary embodiment, magnitude squared wavelet coefficients are computed and scaled to compensate for logarithmic frequency spacing. The output data of the wavelet decomposition circuit is applied to feature extraction circuit 206 and to a circuit 208 that calculates a normalized mid-range energy (NMRE) of the acoustic heart sounds.

Feature extraction circuit 206 receives the signals provided by the wavelet decomposition of circuit 204 and identifies basic heart sounds, clicks and murmurs. In an exemplary embodiment, feature extraction circuit 206 uses Mel cepstrum signal analysis. MEL cepstrum signal analysis is well known in speech analysis. For example, see U.S. Pat. No. 6,725,190 entitled "Method and system for speech recognition features, pitch and voicing with resampled basis functions providing reconstruction of the spectral envelope." The Mel cepstral coefficients may include total energy and first and second differences. Cepstral mean subtraction may be implemented to remove channel differences such as filtering by PCG 202. Features extracted by the MEL cepstrum signal analysis are provided to sequence interpretation circuit 210.

In an alternate embodiment, a feature extraction circuit 206 may use a neural network trained from labeled examples of heart sounds generated by experts in auscultation. The neural network feature extraction circuit 206 is desirably of the time-delay type, where the input layer, number of layers, unit function, and initial weight selection are appropriately chosen using well-known methods. Although a neural network of time-delay type is utilized, it is contemplated that other types of neural networks may be employed.

Sequence interpretation circuit 210 parses the extracted features from feature extraction circuit 206 using a state-transition model of the heart to determine the most probable sequence of cardiac events. The state machine may be a hidden Markov model (HMM) or may be another type of state transition model. The output of sequence interpretation circuit 210 is applied to duration and phase measurement circuit 212.

Duration and phase measurement circuit 212 computes the average state durations of the sequence model, murmur duration and phase alignments. The output data of the duration and phase measurement circuit is applied to NMRE circuit 208 and to murmur detection circuit 214.

NMRE circuit 208 desirably calculates mid-range energy using the wavelet decomposition from time-frequency analysis circuit 204 over the frequency region where the majority of anomalous heart murmurs may be found. A method for computing a NMRE is disclosed in copending U.S. patent application Ser. No. 11/037,665 entitled COMPUTER-ASSISTED DETECTION OF SYSTOLIC MURMURS ASSOCIATED WITH HYPERTROPHIC CARDIOMYOPATHY. Wavelet decomposition scales may correspond to the frequency region of 150-600 Hz or more particularly the range of 206 Hz-566 Hz. The wavelet decomposition scales of interest are summed together over the duration of the heart signal to represent the energy in the bandwidth of interest across the entire recorded heart sound signal.

The energy computed in NMRE circuit 208 may be dependent upon the recording level, signal artifacts, or heart signal transmission strength from the chest wall to PCG 202. NMRE circuit 208 also normalizes the mid-range energy for a desired interval. In an exemplary embodiment, the system normalizes the mid-range energy for each detected systolic and diastolic interval across the sequence of heartbeats. A summary interval energy is then calculated representing median systolic and median diastolic energies across a sequence of heart sounds.

The data provided by NMRE circuit 208 may be shown on graphical display 226. Graphical display 232 may provide the NMRE for a median systolic and a median diastolic interval as energy profiles for the respective intervals.

Murmur detection circuit 214 detects murmurs in the heart sounds according to the output data of the duration and phase measurement circuit 212 and the data received from NMRE circuit 208. In an exemplary embodiment, murmur detection circuit 214 assesses the probability of the presence of a murmur in the heart sounds using HMM matching and the received NMRE according to Bayesian statistics. Murmurs may be further classified relative to systolic/diastolic intervals and may be further labeled with respect to early, mid, late, holo-systolic, holo-diastolic or continuous. Graphical display 226 may be utilized to display the detection results.

The output data of NMRE circuit 208 is applied to a clinical guideline condition referral mapping circuit 216. In addition, any input 228 from medical personnel, regarding dynamic auscultation maneuvers, posture, or recording site may be applied to clinical guideline mapping circuit 216.

Clinical guideline mapping circuit 216 includes systolic characterization circuit 218 that characterizes the median systolic interval based on output data from NMRE circuit 208. Systolic characterization circuit 218 desirably models the median systolic interval according to the energy profile of the median systolic interval. Clinical guideline mapping circuit 216 may also include diastolic characterization circuit 222 that characterizes the median diastolic interval based on output data from NMRE circuit 208. Diastolic characterization circuit 222 desirably models the median diastolic interval according to the energy profile of the median diastolic interval.

Clinical guideline mapping circuit 216 further includes probability circuit 220 that determines the probability that the characterized median systolic interval data corresponds to the first condition or the second condition.

Clinical guideline mapping circuit 216 may further include probability circuit 224 that determines a probability that the characterized median diastolic interval data output from diastolic characterization circuit 222 corresponds to a diastolic murmur condition or an absence of a diastolic murmur condition. Probability circuit 224 may additionally receive the characterized median systolic interval data from systolic characterization circuit 218 and determine a probability that the characterized median systolic and diastolic interval data corresponds to the presence or absence of a continuous murmur condition.

Clinical guideline mapping circuit 216 may alternatively include probability surface circuit 226 that further provides a probability surface of a median systolic interval determined from training data representing the first condition and the second condition. In an exemplary embodiment, the probability surface is a function of a range of normalized mid-range energies and a temporal position within the median systolic interval. Probability surface circuit 226 may also provide a probability surface of a median diastolic interval and/or a median heart beat (systolic and diastolic interval), determined from training data, representing the presence or absence of a diastolic and/or continuous murmur condition.

The data output by the clinical guideline mapping circuit 216, murmur detection circuit 214 and input from user 228 may, alternatively, be provided to summary findings circuit 230. Summary findings circuit 230 may determine a probability of murmurs detected for a subject from heart sounds recorded over all auscultation and/or postures associated with an auscultation protocol. Although not illustrated, summary findings circuit may use a combination of one or more of murmur detection results, median systolic energy, median diastolic energy, a clinical guideline referral probability for the median systolic interval, a diastolic murmur probability, and a continuous murmur probability. An output of summary findings circuit may be displayed on graphical display 232.

The data output by the clinical guideline mapping circuit 216 may be displayed on graphical display 232. Graphical display 232 may show the determined median systolic interval probabilities as a probability representative of the first condition, and/or a probability representative of the second condition. Graphical display 232 may also include the determined median diastolic interval probabilities to provide a probability representative of the presence or absence of a diastolic and/or a continuous murmur condition. The determined probabilities may be shown with a range variance indicative of a confidence measure. Alternatively, the determined median systolic interval derived features may be shown as a probability surface that is a function of systolic interval duration and range of energies along with a focal position of NMRE energy within the median systolic interval. Derived features from median diastolic interval probabilities similarly may be shown on a probability surface except that the probability surface is a function of the diastolic interval durations and range of energies for the median diastolic interval. It is contemplated that continuous murmur probabilities may be similarly presented.

It may be desirable to determine a probability surface of the median diastolic interval to provide a comparison with murmur detection results from murmur detection circuit 214. For example, murmur detection results may not detect the presence of diastolic murmur energy whereas the probability surface may show that murmur is present. Alternatively, murmur detection may over-determine the presence of diastolic murmurs. Furthermore, a NMRE may be computed for any physiological signals where an energy profile may be used according to clinical guideline indicators.

Figure 3:
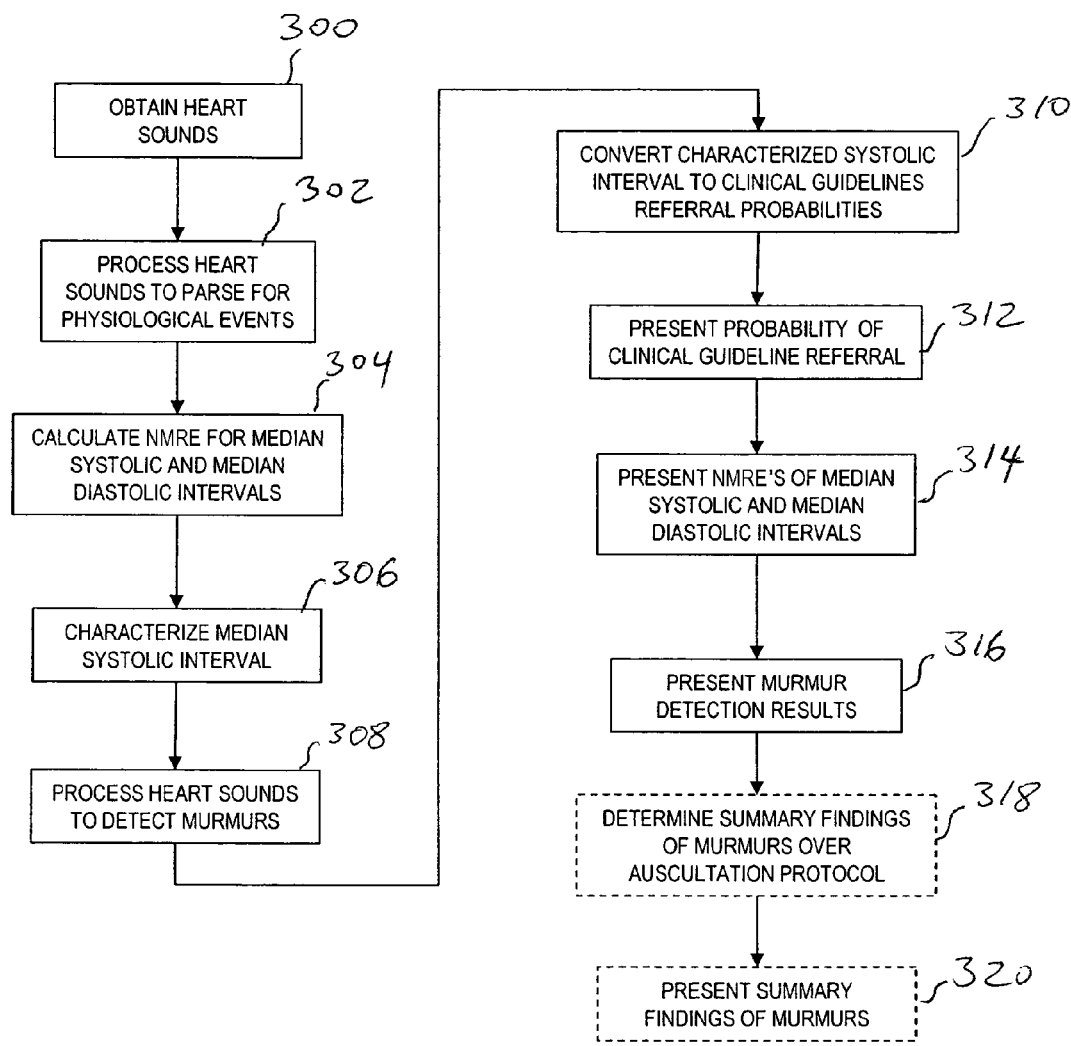
FIG. 3 is a flowchart illustrating an exemplary method for mapping heart sounds to clinical guideline referral conditions according to an aspect of the present invention.

FIG. 3 shows a flowchart illustrating an exemplary method for mapping heart sounds to clinical guideline referral indicators according to the present invention. In step 300, heart sounds are obtained, for example from PCG 202 (FIG. 2). In step 302, the heart sounds are parsed for physiological events. Physiological events may include for example, S1, S2, systolic intervals, diastolic intervals, clicks, split S1, split S2, S3, S4 and ejection sounds. The processing in step 302 may be performed, for example by time-frequency circuit 204, feature extraction circuit 206, sequence interpretation circuit 210 and duration and phase measurement circuit 212 (FIG. 2).

In step 304, NMREs are calculated for a median systolic and a median diastolic interval, for example by NMRE circuit 208 (FIG. 2). In step 306, the median systolic interval is characterized, for example using characterization circuit 218 (FIG. 2). In step 308, the heart sounds are processed to detect murmurs, for example using murmur detection circuit 214 (FIG. 2). In step 310, the characterized systolic interval is converted to clinical guideline probabilities, for example using probability circuit 220 (FIG. 2). It is understood that steps 308 and steps 310 may be sequentially performed in either order or performed concurrently.

Although not shown, it is contemplated that a median diastolic interval may be characterized and converted to diastolic murmur probabilities. The median systolic and median diastolic interval may be used similarly to determine continuous murmur probabilities.

In step 312, the determined clinical guideline referral probability is displayed. In step 314, the NMREs of the median systolic interval and the median diastolic interval are displayed. In step 316, murmur detection results are displayed. The presented data of steps 312, 314 and 316 may be shown on graphical display 232 (FIG. 2). It is understood that steps 312, 314 and 316 may be presented in any order including concurrently.

Alternate step 318 determines summary findings based on a combination of one or more of murmur detection results, median systolic energy, median diastolic energy, a clinical guideline referral probability for the median systolic interval, a diastolic murmur probability, and a continuous murmur probability over all auscultation sites and/or postures representing an auscultation protocol. Summary findings circuit 230 (FIG. 2) may, for example, determine the summary findings. The referral probabilities may additionally include diastolic and/or continuous murmur probabilities, as described above. Alternate step 320 presents the summary findings, for example, on a graphical display 232 (FIG. 2).

The NMREs are desirably presented as energy profiles of the median systolic and diastolic intervals and may assist physicians in making a referral of the patient for more detailed testing. For example, ACC/AHA guidelines for echo referral include having the physician determine if a murmur is present, and whether it is in systole or diastole. If it is in systole, its loudness and profile are analyzed. With auscultation alone, this is done entirely by listening. The presentation of energy profiles provides a graphical means for assertion of murmur presence, location, magnitude and profile.

A physician desirably examines the presented probability (step 312), NMREs of the median systolic and median diastolic intervals (step 314) and murmur detection results (step 316) to determine whether a referral decision may be warranted. In this manner, physiological data are presented according to clinical guideline referral conditions. If the referral probabilities, for example, are borderline between the two conditions (referral and absence of referral indication), the physician may still use murmur detection results and NMRE results. These results may provide more evidence to support or reject a referral indication. The physician is thus presented with auscultatory features analyzed in multiple ways, including according to clinical guidelines, with which to provide assistance with making a referral decision.

Figure 4:
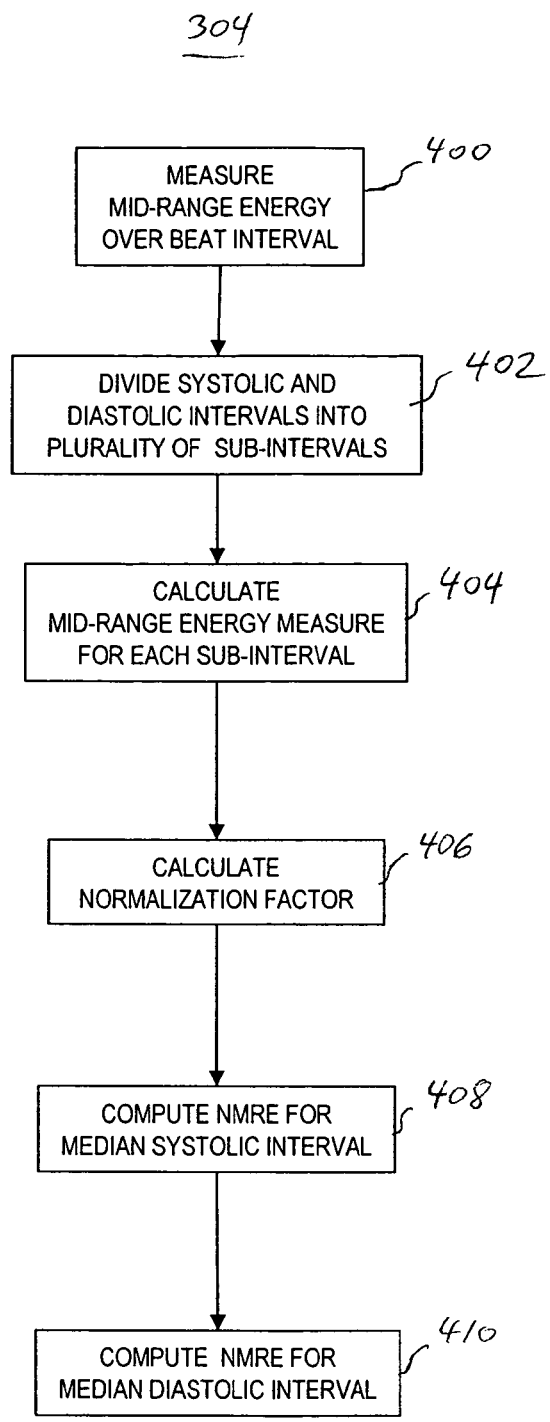
FIG. 4 is a flowchart illustrating an exemplary method for computing normalized energies representative of a median systolic interval and a median diastolic interval of a heart signal according to an aspect of the present invention.

FIG. 4 is a flowchart illustrating an exemplary method for computing normalized energies (step 304 of FIG. 3) representative of a median systolic interval and a median diastolic of a heart signal according to the present invention. In step 400, the resulting heart sound locations from duration and phase measurement circuit 212 (FIG. 2) are parsed to find systolic interval and diastolic interval timestamps from each detected heartbeat. The NMREs as described herein are measured for all detected systolic and diastolic intervals using the parsed timestamps.

In step 402, the systolic and diastolic intervals are divided into multiple subintervals. Subdivision into a plurality of subintervals is used to provide energy profiles of systole and diastole. In an exemplary embodiment, the systolic and diastolic intervals are each divided into thirty subintervals to provide time-normalized windows for the systolic and diastolic intervals. It is contemplated, however, that any number of subintervals that may sufficiently represent the energy profile of systolic and diastolic intervals may be of interest.

In step 404, a subinterval energy is calculated across the sequence of heartbeats. Mid-range energy may be computed as described in NMRE circuit 208 (FIG. 2) over each subinterval duration. Each subinterval across the sequence of heartbeats may be represented by an average value for that subinterval duration. The average value may be computed by the mean, median, frequency, or other methods over the duration of the interval. In an exemplary embodiment, the average value is computed from the median. A median systolic interval and a median diastolic interval are provided from the respective averaged subintervals.

In step 406, a normalization factor is calculated. The normalization factor may be the nominal mid-range energy over the entire heart sound signal. The nominal mid-range energy may be computed from mean energy, median energy, frequency or by other means. In an exemplary embodiment, it is calculated from the median energy and the nominal energy is computed from the same frequency range of interest as for the mid-range energy.

In step 408, a NMRE is then computed for the median systolic interval. The mid-range energy for the median systolic interval is divided by the normalization factor determined in step 406. In step 410, a NMRE is computed for the median diastolic interval. The mid-range energy for the median diastolic interval is divided by the normalization factor determined in step 406. The resulting NMREs for the median systolic and median diastolic intervals may further be presented as a logarithmic ratio or a decibel ratio.

The resulting normalized energy may be converted to a murmur grade based on a correlation between the normalized energy to a standard auscultation murmur grade. For example, a study of a population with heart murmurs, may be undertaken to record and analyze the heart murmurs. The recordings may be further reviewed by a trained cardiologist who may assign a standard murmur grade to the study population. NMREs may then be correlated against the cardiologist's grading of the study population to provide a translation between the NMREs and the murmur grades. The heart murmurs may be reviewed in terms of any of murmur duration, magnitude and frequency spectrum. Psychoacoustics of the heart signal may be taken into account during heart murmur review, such as the murmur appearing to be fainter in the presence of another loud sound.

Figure 5:
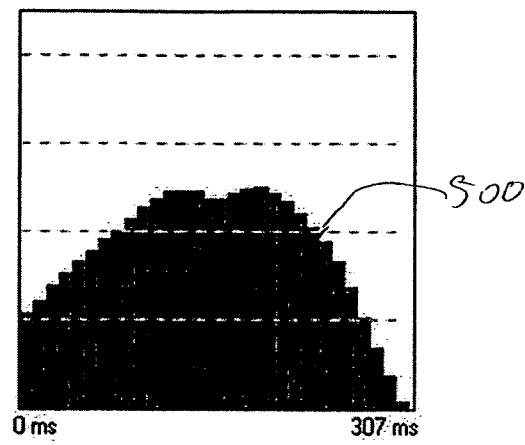
FIG. 5 is an example display of normalized energy representative of a median systolic interval generated using the exemplary method shown in FIG. 4 according to an aspect of the present invention.

After the NMREs are computed they may be presented, for example using graphical display 232 of FIG. 2. NMREs are desirably displayed graphically as bar graphs to illustrate the energy profiles by processing the plurality of subintervals. FIG. 5 illustrates an example display of a normalized energy representative of a median systolic interval when using the exemplary method shown in FIG. 4. FIG. 5 shows energy profile 500 of a median systolic interval. Although not shown, a similar bar graph desirably shows the energy profile of a median diastolic interval. The bar graph may show the energy level by the y axis and time along the x axis. In an exemplary embodiment, the y-axis shows a decibel ratio representative of the NMRE. Alternatively, this ratio may be further converted to a standard auscultation murmur grade.

Figure 6:
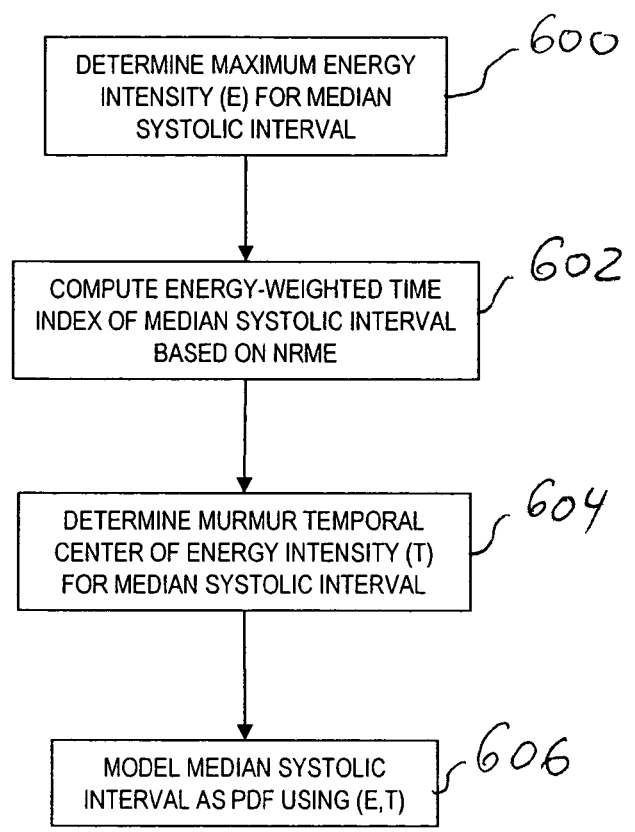
FIG. 6 is a flowchart illustrating an exemplary method for characterizing a median systolic interval according to an aspect of the present invention.

FIG. 6 is a flowchart illustrating an exemplary method for characterizing a median systolic interval (step 306 of FIG. 3) according to the present invention. In step 600, a maximum energy (E) is determined for the median systolic interval from the respective NMRE. In step 602, an energy-weighted time index for the plurality of subintervals representing the median systolic interval is computed based on the respective NMRE. In step 602, each time index may be weighted by an amount of energy in that subinterval.

In step 604, a murmur temporal center of energy intensity (T) is determined for the median systolic interval based on the energy-weighted time index. In step 606, a probability density function (pdf) model of the median systolic interval is generated using the computed (E,T). In an exemplary embodiment, weighted Gaussian mixture models (GMM) are trained to fit a distribution of the median systolic interval from the (E,T) information for the first condition and the second condition. It is understood that the median diastolic interval may be similarly characterized.

GMM is a known in the art method for determining membership of data points in one of the model distributions. The pdf for the first condition and second condition can be represented using a GMM as:

$$P(E, T \mid C1) = \sum_{i=1}^{M} k_{1i} N(E, T \mid \mu_{1i}, \Sigma_{1i}) \quad (1)$$

and $$P(E, T \mid C2) = \sum_{i=1}^{M} k_{2i} N(E, T \mid \mu_{2i}, \Sigma_{2i}) \quad (2)$$

where $P(E,T|x)$ is the pdf, x represents the first condition (C1) or second condition (C2), M is the number of components in the mixture model, $k_x$, is a mixture proportion of component i, and N( ) is a probability distribution function parameterized by $\mu$, mean, and $\Sigma$, the covariance matrix for class x and component i. It is contemplated that the pdf's for the first and second condition may further be modeled according to other factors such as auscultation site and/or posture.

Figure 7:
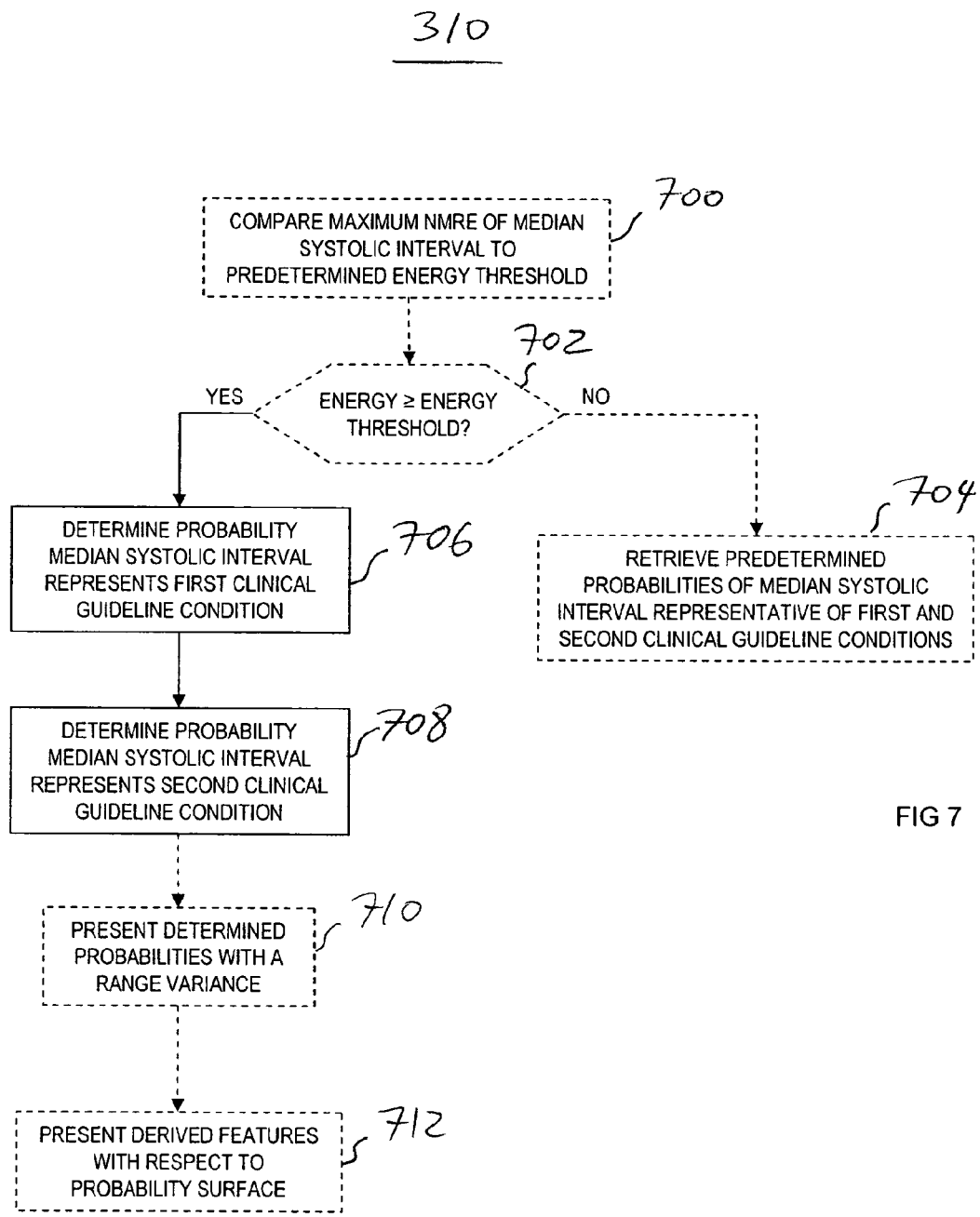
FIG. 7 is a flowchart illustrating an exemplary method for converting a characterized median systolic interval to clinical guideline referral probabilities according to an aspect of the present invention.

FIG. 7 is a flowchart illustrating an exemplary method for converting a characterized median systolic interval into clinical guideline referral probabilities (step 310 in FIG. 3) according to the present invention. In alternative step 700, the maximum NMRE of the median systolic interval is compared to a predetermined energy threshold. In alternate step 702, a decision is made whether the energy is greater than or equal to the predetermined threshold. If the energy is less than the threshold, processing proceeds to alternate step 704. If the energy is greater than or equal to the threshold, processing proceeds to step 706.

If the energy is less than the predetermined threshold, alternate step 702 proceeds to alternate step 704. In alternate step 704, a predetermined probability may be retrieved to indicate that the median systolic interval represents the second condition. The predetermined probability may also be presented as indicating that non-murmur energy was found. In this manner, processing according to alternate steps 700, 702 and 704 may reduce a computational processing cost if the NMRE is a small value, such as being indicative of a non-murmur.

If the energy is greater than or equal to the threshold, alternate step 702 proceeds to step 706. In step 706, a probability is determined that the median systolic interval represents the first condition. In step 708, a probability is determined that the median systolic interval represents the second condition.

In alternate step 710, the determined probabilities are presented including a range variance representative of a confidence measure. The presented probabilities may be associated with the focal point of energy (E,T) of the median systolic interval.

In alternate step 712, derived features from the determined median systolic interval may be presented with respect to a probability surface that is a function of a range of energies and a duration of the median systolic interval.

To determine the probabilities, independent Gaussian distributions, for example, may be generated separately for maximum energy (E) and temporal center (T) from example data representing the first condition and the second condition. In practice, the median systolic interval generated for a heart sound signal may be mapped to the individual (E) and (T) Gaussian distributions and use the independent probabilities based on energy and timing that the median systolic interval is associated with the first and second conditions.

In an exemplary embodiment, the first and second condition spaces are determined and optimized from training the GMM, equations (1) and (2), using example data. In an exemplary embodiment, the GMM include different centers and covariance matrices. The example data is desirably a mixture of referable murmurs, non-referable murmurs and non-murmurs. The example data is desirably classified into the first condition and the second condition by expert listeners. During training, the maximum energy (E) and temporal center (T) of each example are provided as inputs to the GMM. The GMM are desirably trained to match the distribution of positive (first condition) and negative (second condition) training examples. The GMM may then be used to approximate a decision boundary between the first and second conditions.

In practice, the modeled heart sounds from step 606 of FIG. 6 may then be compared to the GMM representing the first condition and the second condition. Probabilities that the heart signal is associated with the first and second conditions may then be determined. These probabilities may be determined for the focal point of the energy (E,T). The probabilities may be presented with a range variance.

In an alternative embodiment, the multiple training examples may be used to derive mean and standard deviation by use provided by a number of experts and merged into a distribution. In a further alternative embodiment, the training data having energy and temporal center (E,T) and received heart sounds may be provided to a neural network to determine whether the median systolic interval of the received heart sounds matches the first condition or the second condition.

In alternative step 712, the probability that the focal center of the median systolic interval is within the first condition may be determined graphically. For example, the focal center may be shown on the probability surface as a point and the probability can be determined directly from the location of this point on the probability surface. In an alternate embodiment, the probability that the focal center is within the first condition may be determined using a lookup table (LUT) having predetermined measured values computed from the probability surface. The focal center may be compared to the LUT values and the closest LUT value may be presented.

Figure 8:
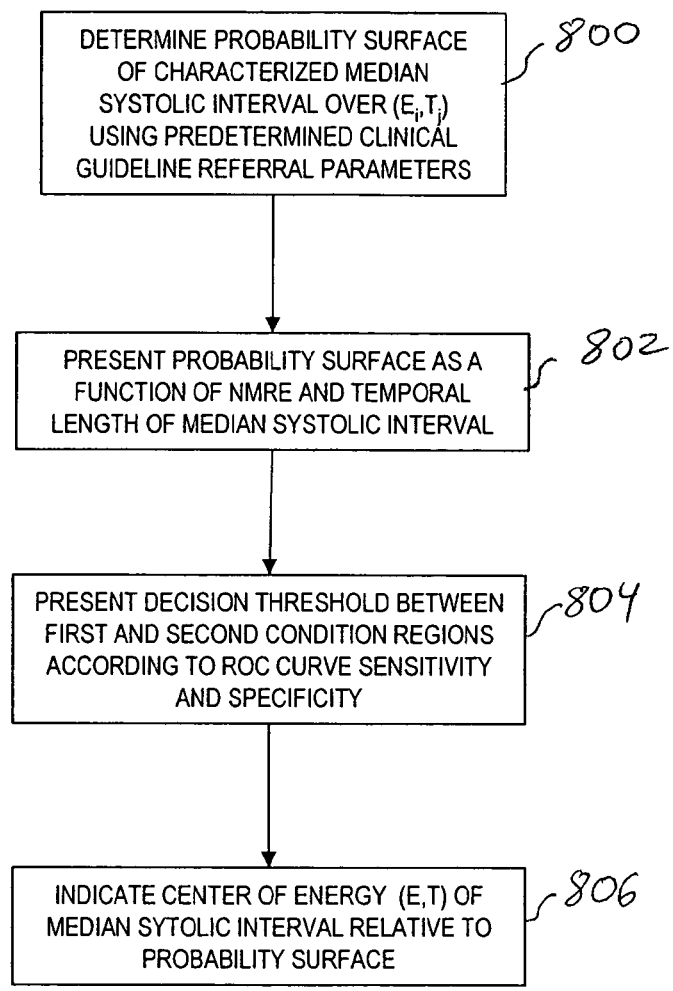
FIG. 8 is a flowchart illustrating an exemplary method for presenting clinical guideline probabilities relative to a probability surface according to an aspect of the present invention.

FIG. 8 is a flowchart illustrating an exemplary method for presenting clinical guideline probabilities relative to a probability surface (step 712 of FIG. 7) according to an aspect of the present invention. In step 800, a probability surface is determined. The model of the received signal is compared against the mixture of Gaussian models representing the first and second conditions over a two-dimensional space representing the normalized duration of the median systolic interval and a range of energies.

Given the GMM of equations (1) and (2) representing the first condition (C1) and the second condition (C2), a posteriori probabilities may be determined from an observation $(E_O, T_O)$ according to the following equation:

$$P(C1 \mid (E_O, T_O)) = \frac{P(E_O, T_O \mid C1)P(C1)}{P(E_O, T_O \mid C1)P(C1) + P(E_O, T_O \mid C2)P(C2)}. \quad (3)$$

After rearranging terms, $$P(C1 \mid E_O, T_O) = \frac{1}{1 + \frac{P(E_O, T_O \mid C2)P(C2)}{P(E_O, T_O \mid C1)P(C1)}} \quad (3a)$$

$$= \frac{1}{1 + \exp[-(\log P(E_O, T_O \mid C1) - \log P(E_O, T_O \mid C2) + \log P(C1) - \log P(C2))]}$$

The a posteriori probability can also be represented as shown in equation (3b):

$$P(C1 \mid E_O, T_O) = \text{sigmoid}[\log P(E_O, T_O \mid C1) - \log P(E_O, T_O \mid C2) + \log P(C1) - \log P(C2)] \quad (3b)$$

The probabilities P(C1) and P(C2) can be estimated, for example, based on information about the prevalence of the first condition and second condition murmurs. Probabilities P(C1) and P(C2) can also be made adjustable to reflect characteristics of individual patients, such as based on age, gender, patient groups or any combination thereof. For example, the a priori probability of young men having an innocent murmur (a second condition murmur) may be lower as compared with the a priori probability for young women in their $3^{rd}$ trimester of pregnancy. In this example, the a priori probability of an innocent murmur for the young men group may be reduced relative to the young women group. As another example, the a priori probability of older adults having a pathological murmur (a first condition murmur) may be higher as compared with the a priori probability for children. In this further example, the a priori probability of the pathological murmur for the older adults group may be increased relative to the children group. The a posteriori probability may also be generated according to other information such as auscultation site and/or posture.

In step 802, the probability surface induced by the Gaussian models is presented as a function of a range of energy and systolic interval duration corresponding to the NMRE and median systolic interval duration. In an exemplary embodiment, the probability surface is presented as a contour map representing the probability that the first condition (associated with a referral indication) is present.

In step 804 a receiver operating characteristic (ROC) curve can be derived from the first and second condition probabilities for the training data. An operating point may be selected on the ROC curve to determine a decision boundary between the first condition and the second condition according to a desired sensitivity and specificity. It is desirable to reduce false positives without increasing false negative. Thus, in an exemplary embodiment, the sensitivity and specificity are selected to be 95% and 80%, respectively. The decision boundary represents the referral probability threshold used to achieve the selected performance. It is understood that these sensitivities and specificities are not meant to be limiting. Any desired sensitivity and specificity may be used to compute the threshold. The decision boundary is desirably presented between the first and second conditions on the probability surface In step 806, the focal center of energy for the median systolic interval (step 306 of FIG. 3) is presented as a point on the probability surface. The position of this point on the probability surface indicates the probability that the detected anomaly corresponds to the first condition.

Figure 9:
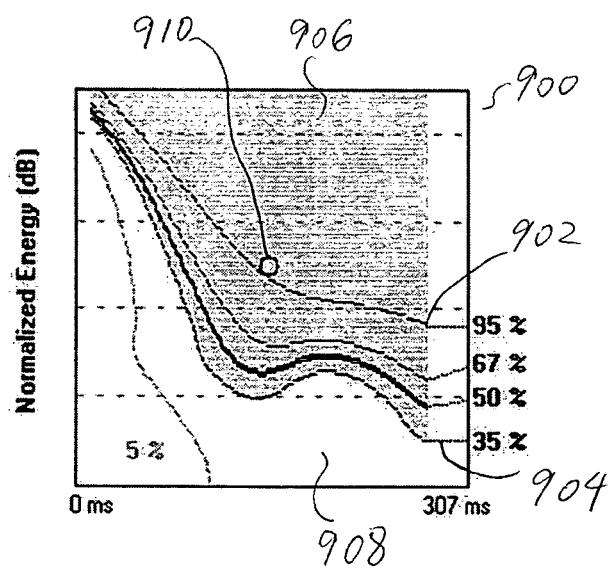
FIG. 9 is an example display of clinical guideline probabilities relative to a probability surface using the normalized energy of FIG. 5 and the exemplary method shown in FIG. 8.

FIG. 9 illustrates an example display of clinical guideline probabilities relative to probability surface 900. Probability surface 900 is determined using the NMRE of FIG. 5 and the exemplary method shown in FIG. 8. Probability surface 900 includes a plurality of contours such as 902 representing the probability that the median systolic interval represents the first condition (a referral indication). A decision boundary 904 determined for a sensitivity and a specificity illustrates a boundary between the first condition, region 906 above boundary 904 and the second condition, region 908 below boundary 904. Region 906 or 908 may be highlighted to further distinguish the two conditions.

Probability surface 900 is desirably presented as a function of median systolic interval duration and a range of energies computed from the NMRE of the median systolic interval. Probability surface further includes focal center of energy position 910 representing the focal center (E,T) in normalized mid-range energy and time of the median systolic interval. In this manner, a physician may readily determine the probability that the detected anomaly corresponds to a referral indication based upon its position relative to one of the contours 902.

Presentation of the focal center 910 on the probability surface 900 may provide a confidence measure regarding the location of focal center 910 within region 906. The physician may immediately judge whether focal center 910 has a high probability of referral, a borderline or low probability of referral. The physician can judge the sensitivity of the probability measure to small changes in energy or timing. For example, if the focal center 910 is on the leftmost edge of region 906, a small change in timing may substantially change the probability. If the focal center 910 is in a plateau portion of the contours 902 and in region 906, the probability may be relatively insensitive to timing changes in the focal point 910.

Figure 10:
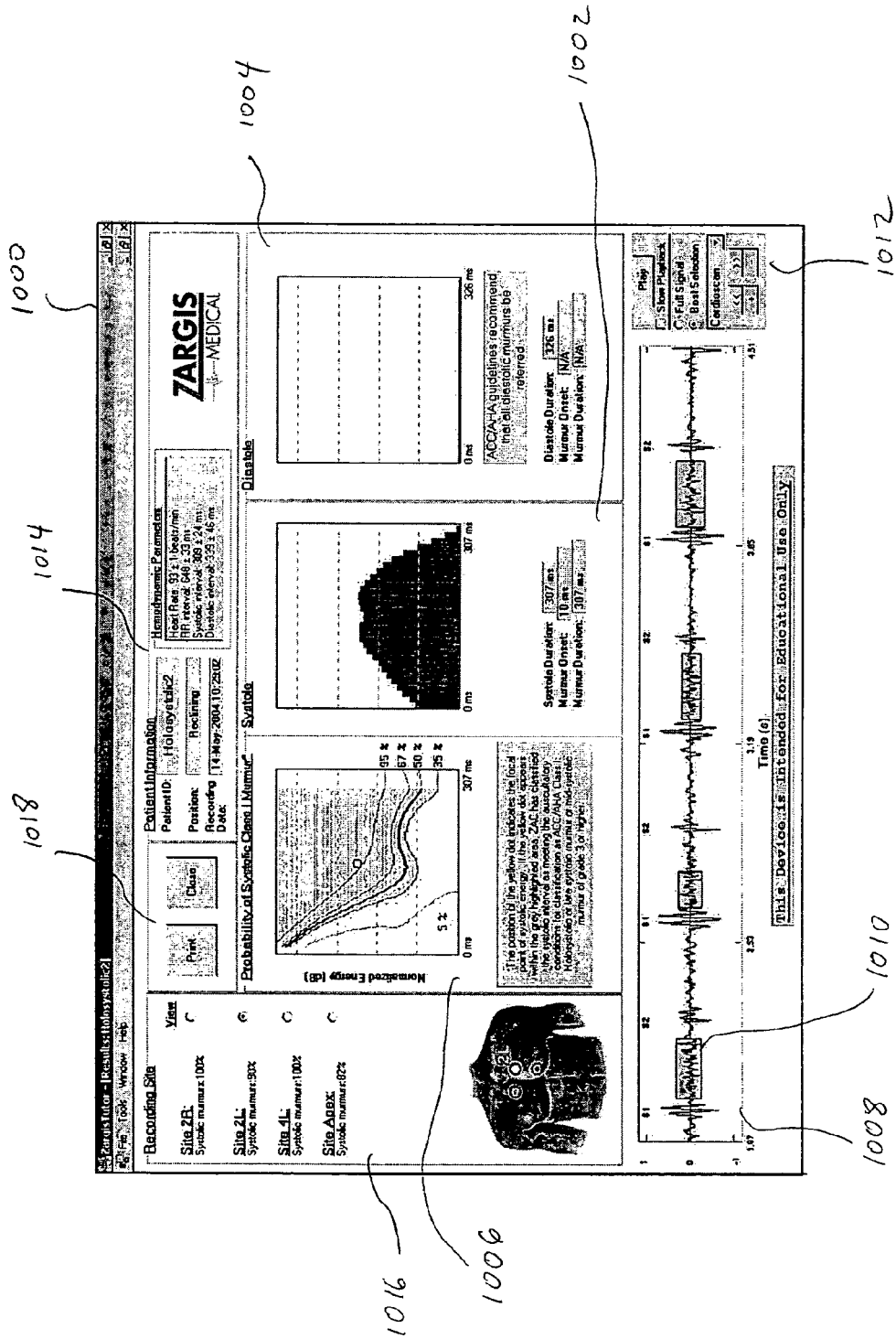
FIG. 10 is an example display of the exemplary system shown in FIG. 2 that employs an embodiment of the present invention.

FIG. 10 is an example display 1000 of exemplary system graphical display 232 shown in FIG. 2 that employs an embodiment of the present invention. Display 1000 desirably includes NMRE display 1002 for the median systolic interval and NMRE display 1004 for the median diastolic interval. As described above, guidelines for referral include any indication of a diastolic murmur. It is thus desirable to include NMRE display 1004. Display 1000 also includes probability surface map 1006 to provide clinical guideline referral indication for systolic murmurs.

NMRE displays 1002 and 1004 may include information associated with the respective median systolic and diastolic intervals. Such information may include the interval duration, a murmur onset time and a murmur duration time, as well as clinical guideline information. NMRE displays 1002 and 1004 may additionally illustrate the energy profile to highlight regions suspected to contain murmurs by murmur detection circuit 214 (FIG. 2). For example, regions suspected to contain murmurs may be colored differently from the NMRE results (for example, from NMRE circuit 208 of FIG. 2).

An audio signal display 1008 desirably includes annotated heart sounds such as S1 and S2. Murmur detection display 1010 may include highlighting such as enclosing within a box regions of the audio signal suspected to contain murmurs. A probability of murmurs detected (not shown) may also be displayed.

Although not shown, it is contemplated that display 1000 may include a summary findings indicator that summarizes the presence of murmurs over an auscultation protocol. The summary findings indicator may present results from summary findings circuit 230 (FIG. 2) that may use a combination of one or more of murmur detection results, median systolic energy, median diastolic energy, a clinical guideline referral probability for the median systolic interval, a diastolic murmur probability, and a continuous murmur probability.

A physician may use NMRE displays 1002 and 1004, audio signal display 1008 with murmur detection display 1010 and probability surface 1006 to make a referral decision. If, for example, a continuous murmur is present and illustrated in audio signal display 1008 but is illustrated in probability surface map 1006 as being in the non-referable region, the presented data may provide the physician with additional information for making an appropriate referral decision based on other parameters (e.g. EKG, heart rate, audio signal display 1008).

Display 1000 may further include audio signal indicators 1012 to allow review of audio signal 1008. Indicators 1012 may include a slower audio playback suitably processed to maintain the same pitch/frequency content of the audio signal. Slower playback may provide a more detailed listening analysis of a desired heart sound. Indicators 1012 may also include a position indicator (not shown) such as a vertical bar on audio signal display 1008 indicating the current audio playback location within the audio signal. Indicators 1012 may further include playback volume control.

Indicators 1012 may allow for the display and navigation through portions of audio signal display 1008. Indicators 1012 may include scroll bars for panning forward and backward relative to a currently displayed portion. Indicators 1012 may also include controls for expanding and contracting the portion of the signal that is displayed.

Display 1000 may include patient information 1014 including hemodynamic parameters computed by exemplary system 200. Hemodynamic parameters may include a heart rate, an RR interval, a systolic interval duration and a diastolic interval duration. One or more of the hemodynamic parameters may be presented including a mean and a variance. Patient information 1014 may also include recording posture, patient identification such as an identification number, age and/or gender as well as the date of recording.

Display 1000 may include recording site indicators 1016 which indicate the recording location relative to standard auscultation locations, such as 2R, 2L, 4L and apex locations. Recording site indicators 1016 may include links to data analyzed for other recording sites for the patient. Selecting a link may present a display similar to display 1000 except that the results are processed for the selected recording site.

Display 1000 may include options 1018 for generating a hardcopy printout of display 1000 or for closing the display.

Although the invention has been described as apparatus and a method, it is contemplated that it may be practiced by a computer configured to perform the method or by computer program instructions embodied in a computer-readable carrier such as an integrated circuit, a memory card, a magnetic or optical disk or an audio-frequency, radio-frequency or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method for assisting in a referral indication of heart murmurs, the method comprising the steps of:
    receiving an acoustic signal representing heart sounds;
    parsing the received acoustic signal into predetermined physiological events including a plurality of systolic intervals and a plurality of diastolic intervals;
    computing a first normalized mid-range energy representative of a median systolic interval and a second normalized mid-range energy representative of a median diastolic interval, respectively, the first and second normalized mid-range energies computed from the parsed acoustic signal;
    characterizing the median systolic interval based on the first normalized mid-range energy by computing a focal point of energy using a maximum first normalized mid-range energy and systolic interval temporal center of a normalized mid-range energy concentration to generate a model of the median systolic interval;

determining probabilities relative to a first condition associated with the referral indication and a second condition associated with an absence of the referral indication based on the characterized median systolic interval; and presenting the first normalized mid-range energy, the second normalized mid-range energy and the determined probabilities, whereby the presented first normalized mid-range energy, the second normalized mid-range energy and the determined probabilities may be used to determine whether the referral is indicated.

2. The method according to claim 1, the method including the steps of:

characterizing the median diastolic interval based on the second normalized mid-range energy;

determining further probabilities relative to a diastolic murmur condition and a non-diastolic murmur condition; and the step of presenting further includes presenting the further determined probabilities.

3. The method according to claim 1, wherein the first and second normalized mid-range energies are each between 150 and 600 Hz.

4. The method according to claim 1, wherein the first and second normalized mid-range energies are converted to respective murmur grades and the step of presenting the first and second normalized mid-range energies presents the respective murmur grades.

5. The method according to claim 1, wherein the first condition includes systolic murmurs selected from the group consisting of a holo-systolic murmur, a late-systolic murmur and a mid-systolic murmur equal or greater than a murmur grade 3.

6. The method according to claim 1, wherein the step of presenting the determined probabilities presents derived features relative to a probability surface, the probability surface including a first region representing the first condition and a second region representing the second condition.

7. The method according to claim 6, wherein the probability surface includes a predetermined threshold between the first region and the second region, the predetermined threshold selected according to a predetermined sensitivity and a predetermined specificity.

8. The method according to claim 7, wherein the probability surface is presented as a function of a duration of the median systolic interval and the first normalized mid-range energy associated with the median systolic interval.

9. The method according to claim 1, the step of computing the first normalized mid-range energy and second normalized mid-range energy includes the steps of:

dividing each of the median systolic interval and median diastolic intervals into a plurality of subintervals; and calculating the first normalized mid-range energy and second normalized mid-range energy for each of the sub-intervals of the respective median systolic interval and median diastolic interval.

10. The method according to claim 9 wherein:

the step of dividing each of the median systolic interval and median diastolic intervals into a plurality of subintervals includes the steps of:

subdividing the median systolic interval into at least thirty intervals;

subdividing the median diastolic interval into at least thirty intervals, and the step of presenting the first and second normalized mid-range energies includes the step of graphically displaying the calculated normalized mid-range energy for each of the plurality of sub-intervals.

11. The method according to claim 1, including the step of detecting heart murmurs using the parsed audio signal and the first normalized mid-range energy and second normalized mid-range energy.

* * * * *

UNITED STATES PATENT AND TRADEMARK OFFICE
CERTIFICATE OF CORRECTION

Page 1 of 1

PATENT NO. : 8,690,789 B2
APPLICATION NO. : 13/103750
DATED : April 8, 2014
INVENTOR(S) : Raymond L. Watrous It is certified that error appears in the above-identified patent and that said Letters Patent is hereby corrected as shown below:

In the Specification

<u>Column 12</u>

Line 1, delete "$k_x$," and insert -- $k_{xi}$ --, therefor.

<u>Column 13</u>

Line 58, delete "$T_OC1)$" and insert -- $T_O|C1)$ --, therefor.

Signed and Sealed this
Second Day of December, 2014

Michelle K. Lee
*Deputy Director of the United States Patent and Trademark Office*